United States Patent [19]

Uranishi

[11] 4,240,295
[45] Dec. 23, 1980

[54] ULTRASONIC DIAGNOSING APPARATUS

[75] Inventor: Michiyoshi Uranishi, Tokyo, Japan

[73] Assignee: Tokyo Shibaura Denki Kabushiki Kaisha, Japan

[21] Appl. No.: 958,692

[22] Filed: Nov. 8, 1978

[30] Foreign Application Priority Data

Nov. 10, 1977 [JP] Japan ............... 52-134983

[51] Int. Cl.³ ............................................ G01N 29/00
[52] U.S. Cl. .................................... 73/607; 128/660
[58] Field of Search ............... 73/606, 607, 609, 610, 73/611, 612, 618, 619, 620, 621, 624, 625, 626; 128/660; 340/5 MP; 367/7

[56] References Cited

U.S. PATENT DOCUMENTS

| 3,555,888 | 1/1971 | Brown | 128/660 |
| 3,856,985 | 12/1974 | Yokoi et al. | 128/660 |
| 4,010,634 | 3/1977 | Baumgartner | 73/620 |

FOREIGN PATENT DOCUMENTS 135885 10/1975 Japan .
148984 12/1977 Japan .

OTHER PUBLICATIONS

M. Nakashika et al., "Recent Ultrasonic Tomographic System," Toshiba Review, No. 82, pp. 13–18, Jun. 1973.
H. Yokoi et al., "C-Mode Method for Obtaining a Plane Image at a Desired Depth," Japanese Ultrasonic Medical Society, pp. 131–132, 1974–1976.
D. N. White, "Ultrasound in Medical Diagnosis", Chapter 5, pp. 271–276, 1976.

Primary Examiner—Stephen A. Kreitman
Attorney, Agent, or Firm—Finnegan, Henderson, Farabow, Garrett & Dunner

[57] ABSTRACT

An ultrasonic diagnosing apparatus displays a modified C-mode image of the target of an object to be diagnosed by mechanically moving an ultrasonic probe around the target portion while electronically driving the probe to scan the target. The ultrasonic diagnosing apparatus comprises a circuit for setting a desired cross-section to be diagnosed in the B-mode image of the target while observing said B-mode image, a memory for storing the data of the cross-section set by the cross-section setting circuit, a function generator for converting the position data into a function signal for controlling the scanning of the target and the processing of an ultrasonic echo signal reflected therefrom, a signal processing device for processing the ultrasonic echo signal under control of the function signal, and a display means for displaying a modified C-mode image of the target.

15 Claims, 20 Drawing Figures

ULTRASONIC DIAGNOSING APPARATUS

BACKGROUND OF THE INVENTION

The invention relates to an ultrasonic diagnosing apparatus with an ultrasonic probe of the electronic linear scanning type.

In the conventional ultrasonic diagnosing apparatus of this type, scanning is performed by mechanically moving an ultrasonic probe on a plane which is spaced a fixed distance from and positioned parallel with the abdominal surface of the subject to be examined. In the conventional apparatus an ultrasonic beam directed orthogonal to the abdominal surface and reflected from the target portion to be diagnosed in the abdomen. The tomogram (C-mode image) thus formed is a cross-sectional image of the target area taken along a plane which is spaced a fixed distance from and is in parallel with the scanning surface of the ultrasonic probe.

Organs in the abdomen such as the kidney and the liver take various shapes as cross-sections are oriented in various directions, and this fact is correspondingly applicable for the target portion to be diagnosed. Nevertheless, the C-mode tomogram formed by the conventional apparatus is a mere two-dimensional cross-sectional image of the target portion taken parallel with the abdominal surface. Therefore, it is very difficult to accurately diagnose the desired target portion.

SUMMARY OF THE INVENTION

Accordingly, an object of the invention is to provide an ultrasonic diagnosing apparatus which is capable of displaying a modified C-mode image of the target portion taken along a selected cross section of the target portion.

The ultrasonic diagnosing apparatus according to the invention is of the linear electronic scanning type. In order to display a modified C-mode image of the target portion of an object to be diagnosed, the target portion is electrically scanned by means of an ultrasonic probe while the probe is mechanically moved in a desired direction.

The ultrasonic diagnosing apparatus includes a circuit for setting a desired cross section to be observed in the B-mode image of the target portion, a memory for storing the position data of the cross-section set by the cross-section setting circuit, a function generator for converting the position data into a function signal for controlling the scanning of the target portion and the processing of an ultrasonic echo signal reflected therefrom, a signal processing device for processing the ultrasonic echo signal under control of the function signal, and a display device for displaying a modified C-mode image of the target portion.

With such an arrangement of the ultrasonic diagnosing apparatus, an operator can accurately diagnose the target portion in the object.

Other objects, features and advantages of the invention will be apparent from the following description taken in connection with the accompanying drawings, in which:

DETAILED DESCRIPTION OF THE PREFERRED EMBODIMENT

Figure 1:
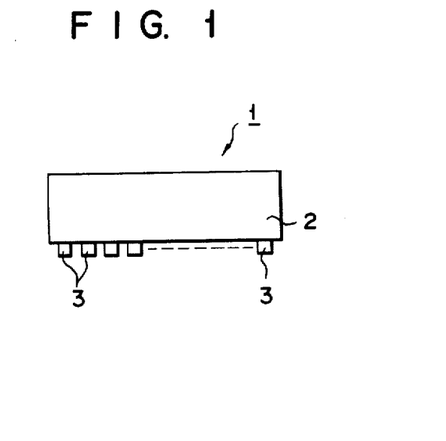
FIG. 1 schematically illustrates the front side of a probe of the electronic scanning type which is used in the invention.
Figure 2:
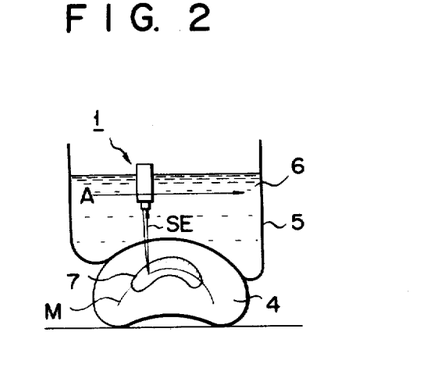
FIG. 2 schematically illustrates a state that the abdomen of a human body is scanned by the probe in FIG. 1.

As shown in FIG. 1, an ultrasonic probe 1 of the electronic scanning type comprises a damper member 2 and a series of transducers 3 longitudinally disposed at the bottom of the damper member 2. In the scanning of the target portion, more strictly the target area, of an object to be diagnosed such as an organ in the abdomen of a human body, the probe 1 is generally mechanically moved, as shown in FIG. 2. The ultrasonic probe, as viewed from one of the sides thereof, is dipped in ultrasonic transmissible medium 6 such as water or liquid paraffin contained in a flexible bath 5 which is placed on the abdomen 4 when it is diagnosed. As shown, the probe is disposed so that the ultrasonic radiating side of it faces toward the abdomen 4 and is moved in the medium 6 in the direction indicated by an arrow A by means of a mechanical scanning unit (not shown). An ultrasonic wave radiated from the transducer 3 of the probe 1 is reflected by an area of the target portion 7 and travels toward the transducer 3 as an ultrasonic echo designated by SE. The transducers of the probe 1 are divided into several blocks each including a plurality of adjacently disposed transducers. These transducers and blocks are successively excited to radiate ultrasonic beams toward the object 4. That is to say, the electronic scanning is performed in this manner. The tomogram of the target area is accordingly defined by the scanning range of the electronic scanning and the movement range of the probe 1 when it is moved in the direction A.

Assume now that the target portion 7 of the organ to be diagnosed is curved against the probe movement direction A, as shown in FIG. 2. In this case, the image of the target portion 7 necessary for its diagnosis must be C-mode a tomogram of the cross section taken along the line M of the target portion 7. The C-mode tomogram is formed by processing the ultrasonic echoes SE reflecting from the target area extending along the line M when the probe 1 is mechanically moved in the direction M while electronically scanning the target portion 7. The echo signals are displayed by a display device including a cathode ray tube (hereinafter referred to as CRT).

Figure 3:
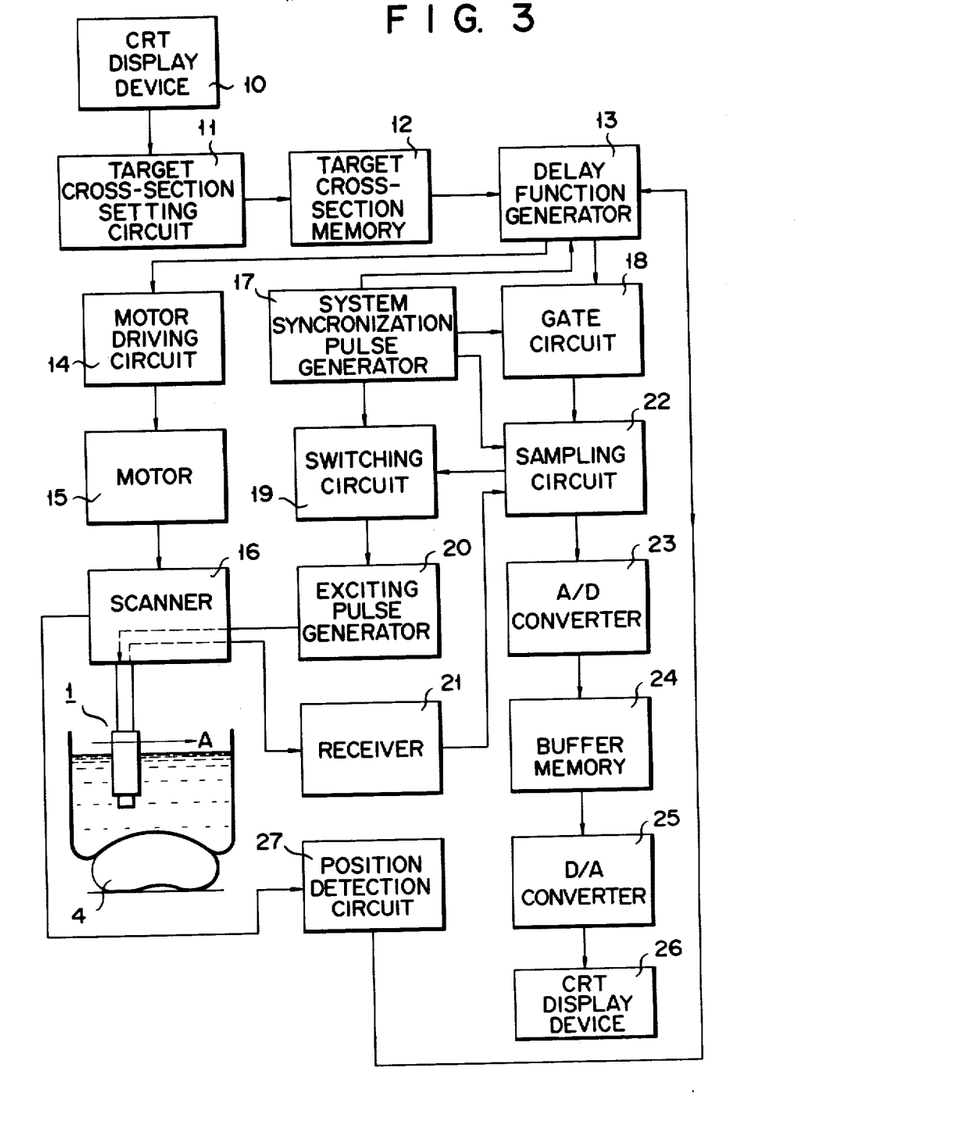
FIG. 3 shows a block diagram of an embodiment of the ultrasonic diagnosing apparatus according to the invention.

Turning now to FIG. 3, there is shown an ultrasonic diagnosing apparatus of the invention which is capable of displaying a C-mode tomogram of any cross section of the target portion 7. In the figure, reference numeral 10 designates a conventional display device including a CRT for displaying a B-mode image of the target area of the portion 7. A target cross-section setting circuit designated by 11 is used to set a desired target area of the portion 7, i.e. the cross section taken along the line M. The cross-section setting circuit 11 may be a light pen or a potentiometer. A memory 12 stores a signal designating the desired target area produced by the setting circuit 11. In other words, data of the curve M shown in FIG. 2, for example, are stored in the memory circuit 12. In a delay function generator 13, the data of the respective positions on the curve read out from the memory 12 are converted into a function signal with a predetermined delay of time representing the diagnostic area of the target portion 7 in accordance with actual positions of the probe 1. A motor driving circuit 14 operates in response to the function signal corresponding to the positions on the curve M. A motor 15, which is driven by the output signal from the motor driving circuit 14, moves the probe 1 in the direction A through a scanner 16. A position detection circuit 27 produces the position signal of the probe 1 electrical information regarding the actual position is to the delay function generator 13. A system synchronization pulse generator 17 produces a system synchronization signal in order for the probe 1 to electrically scan the target plane. The system synchronization signal is also supplied to the delay function generator 13, a gate circuit 18 and a sampling circuit 22 to process the ultrasonic echo signal reflected from the target as described herein after. The gate circuit 18 is enabled by the function signal from the function generator 13 to selectively permit the system synchronization signal from the generator 17 to pass therethrough. A switching circuit 19 selectively switches the transducers in the probe 1 to be excited by an exciting pulse generator 20. The exciting pulse generator 20 applies exciting pulse signals to the transducers in synchronism with the generation of the system synchronization pulse. Upon receiving the pulse signals, the transducers radiate the ultrasonic wave toward the target. The transducers convert the ultrasonic echoes reflected from the target area into an electrical signal. The electrical signal is supplied to a receiver 21 by which the electrical signal is amplified. A sampling circuit 22 samples the output signals of the receiver 21 in response to the delay function signal delivered through the gate circuit 18. An analog to digital converter 23 converts the signal into a digital signal. A buffer memory 24 temporarily stores the digital signal converted. A digital to analog signal converter 25 converts the digital signal read out from the buffer memory 24 into the corresponding analog signal. The CRT display device 26 displays the analog signal in the form of a modified C-mode image.

The operation of this ultrasonic diagnosing apparatus will be described hereinafter.

The conventional ultrasonic diagnosing device may be used for displaying a B-mode image of the target on the CRT display device 10. In this embodiment, the CRT display device 10, the motor driving circuit 14, the motor 15, the scanner 16, the probe 1, the flexible bath 5, and the position detection circuit 27 are used for those of the conventional ultrasonic diagnosing device. While observing the B-mode image, an operator traces the curve M so as to designate the desired target area of the target portion 7 by operating the target cross-section setting circuit 11. The output signal of the target cross-section setting circuit 11 is supplied to the memory 12. The memory 12 stores the data of the desired target area. In this manner, after the setting of the target cross-section area to be observed is completed, the probe 1 is driven to scan it from the given position. At this time, the actual position of the probe 1 is detected by the position detection circuit 27, and electrical information regarding the actual position is then delivered to the delay function generator 13. Upon receipt of the position signal, the delay function generator circuit 13 reads out the data of the desired target plane from the memory 12. The delay function generator 13 produces a function signal, the initiation timing of which is delayed from that of respective system synchronization pulses by a propagation time of both ways between the transducers and the actual position of the target portion. The delay function signal is applied as a control signal to the gate circuit 18 and the motor driving circuit 14.

Figure 4A:
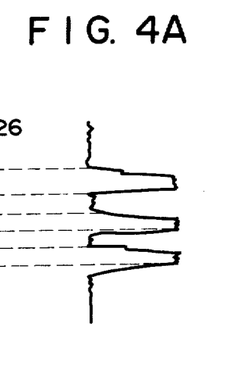
FIG. 4A show a wave form of an ultrasonic echo reflected from the target area of an object to be diagnosed.
Figure 4B:
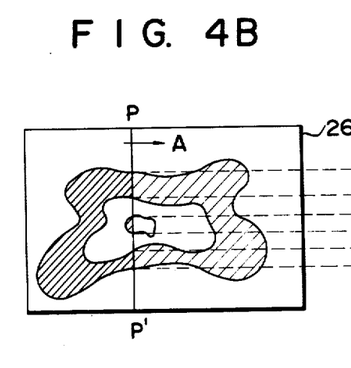
FIG. 4B shows a tomogram formed by the ultrasonic echo shown in FIG. 4A.

The exciting pulse circuit 20 applies a pulse signal to the transducers of the probe 1 in synchronism with the system synchronization pulse derived from the generator 17. Every time the transducers receive the exciting pulse signal, the transducers radiate ultrasonic waves toward the target area. The ultrasonic echoes are reflected from areas with a different acoustic impedance and return to the probe 1. The ultrasonic echoes are converted into electrical signals by transducers of the probe 1, which are applied to the sampling circuit 22 through the receiver 21. The system synchronization pulse generator 17 provides the sampling circuit 22 with sampling instruction signals through the gate circuit 18 which is under control of the delay function signal from the circuit 13. Accordingly, the sampling circuit 22 samples the electrical signals representing the configuration of the target plane. As the sampled signals are in the form of discrete analogue signals, they are converted into digital signals by the A-D converter 23 so that they are temporarily stored in the buffer memory 24 to form resultant video data regarding the selected C-mode cross-section image of the target area. The data derived from the buffer memory 24 are converted again into the analog signals by the D-A converter 25. FIG. 4A shows schematically the analog signals in converter 25 to corresponding to a cross-section taken along line P-P' shown in FIG. 4B. The analogue signals are then applied to the CRT display device 26 which displays the image of the target plane as shown in FIG. 4B.

Figure 5:
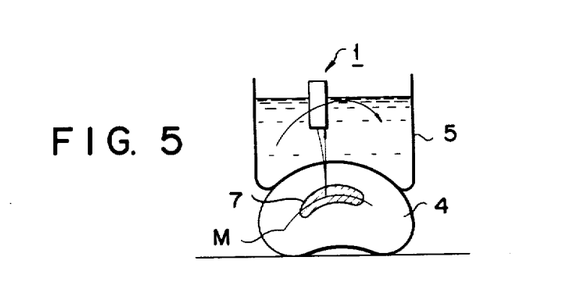
FIGS. 5 and 6 schematically illustrate other acceptable movements of the probe.
Figure 6:
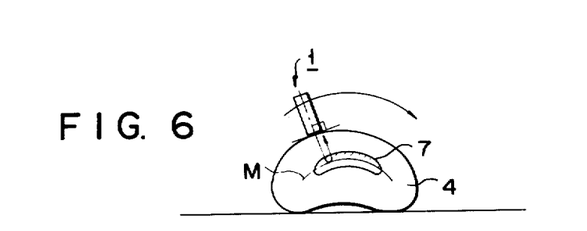

The probe can be moved across the target area in several manners. As shown in FIG. 5, the scanner 16 may move the probe 1 in a curve parallel to curve M. Another acceptable modification is to keep the scanner 16 in contact with the surface of the abdomen as shown in FIG. 6.

A second embodiment of the invention will be given with reference to FIG. 7 in which like numerals are used to designate like parts or portions discussed in reference to FIG. 3. A switch circuit 30 switches between a line permitting an exciting pulse from an exciting pulse generator 20 to go to the transducer elements of the probe 1 and another line permitting echo signals reflected from the target portion to be diagnosed to go to a receiver 21. An amplifier intervening between the receiver 21 and a switch 32 and designated by numeral 31 amplifies the echo signal, i.e. video signal, from the receiver 21. In the FIG. 3, the amplifier 31 is included in the receiver 21.

A switch 32, under control of a switch control means 33, selects either the signal path extending to a CRT display device 26 for displaying the modified C-mode image of the target area or the signal path extending to another CRT display device 10 for displaying the B-mode image. When the movable contact of the switch 32 is turned to a contact I, the video signal from the amplifier 31 is transferred to the CRT display 10. When it is turned to a contact II, the video signal reaches the CRT display device 26.

A position calculation circuit 34, which is connected to a probe position detection circuit 27, receives position signals representing a position of the probe I to calculate the relative position (Xp, Yp) of the probe 1. The X-position signal Xp and Y-position signal Yp are delivered from the position calculatiion circuit 34 to an arithmetic operation circuit 35 where $\sqrt{Xp^2+Yp^2}$ signal is calculated. $\sqrt{Xp^2+Yp^2}$ is defined as the amount of movement of the probe 1 from the previous position of the probe 1 to the position (Xp, Yp) thereof. The $\sqrt{Xp^2+Yp^2}$ signal from the arithmetic operation circuit 35 is converted into a digital signal by an A-D converter 36. In a digital comparator 37 which is connected at the input to the A-D converter 36 and at the output to one input terminal of an AND gate 18, comparison is made between the $\sqrt{Xp^2+Yp^2}$ signal and a reference signal indicative of a reference distance which determines the resolution of a modified C-mode image to be displayed by the CRT display device 26. Particularly, only lower several digits of $\sqrt{Xp^2+Yp^2}$, which are substantially indicative of an actual amount of movement of the probe 1, are compared with the reference signal.

Thus, comparison is made substantially between the amount of slight movement of the probe 1, designated by the lower several digits and the reference distance of the reference signal, and when these are coincident, the comparator 37 generates an output signal. Thus, each time that the probe 1 is mechanically positioned at the reference distance which determine the resolution of the modified C-mode image, the output signal is generated from the comparator 37.

The Xp signal of the position calculation circuit 34 is also supplied to an X-sweep signal generator 46. The generator 46, upon receipt of the Yp signal, generates an X-sweep signal which is supplied to a scan converter 43. Similarly, the Yp signal is supplied to a Y-sweep signal generator 47. Upon receipt of the Yp signal, the generator 47 generates a Y-sweep signal which is applied to the scan converter 43.

The target cross-section setting circuit 11 includes a sine-cosine potentiometer to produce a target cross-section signal which is supplied to an analog memory 39 and stored therein. The analog memory 39, however, may be replaced by a series combination of an analog to digital converter for receiving the output signal of the target cross-section setting circuit 11 and converting the corresponding digital signal, a digital memory for storing the digital signal and a digital to analog converter for converting the digital signal read out from the memory into an analog signal. The signal stored in the memory 39 is read out in synchronism with the system synchronization pulse signal and supplied to a comparator 38. To the comparator 38 is further applied a saw-tooth wave signal derived from a saw-tooth wave signal generator 40. These signals are compared by the comparator 38 and when these are coincident in level, it produces an output signal. A pulse shaper 41 is provided to effect the wave-shaping of the signal from the comparator 38. A switch circuit 42 selectively applies the video signal from the amplifier 31 and the target cross-section setting signal from the wave shaper 41 to a scan converter 43. The scan converter 43 temporarily stores and converts the selected signal into a suitable B-mode signal in accordance with the X- and Y-sweep signals from the X-and Y-sweep signal generators 46 and 47, respectively.

Figures 13, 14:
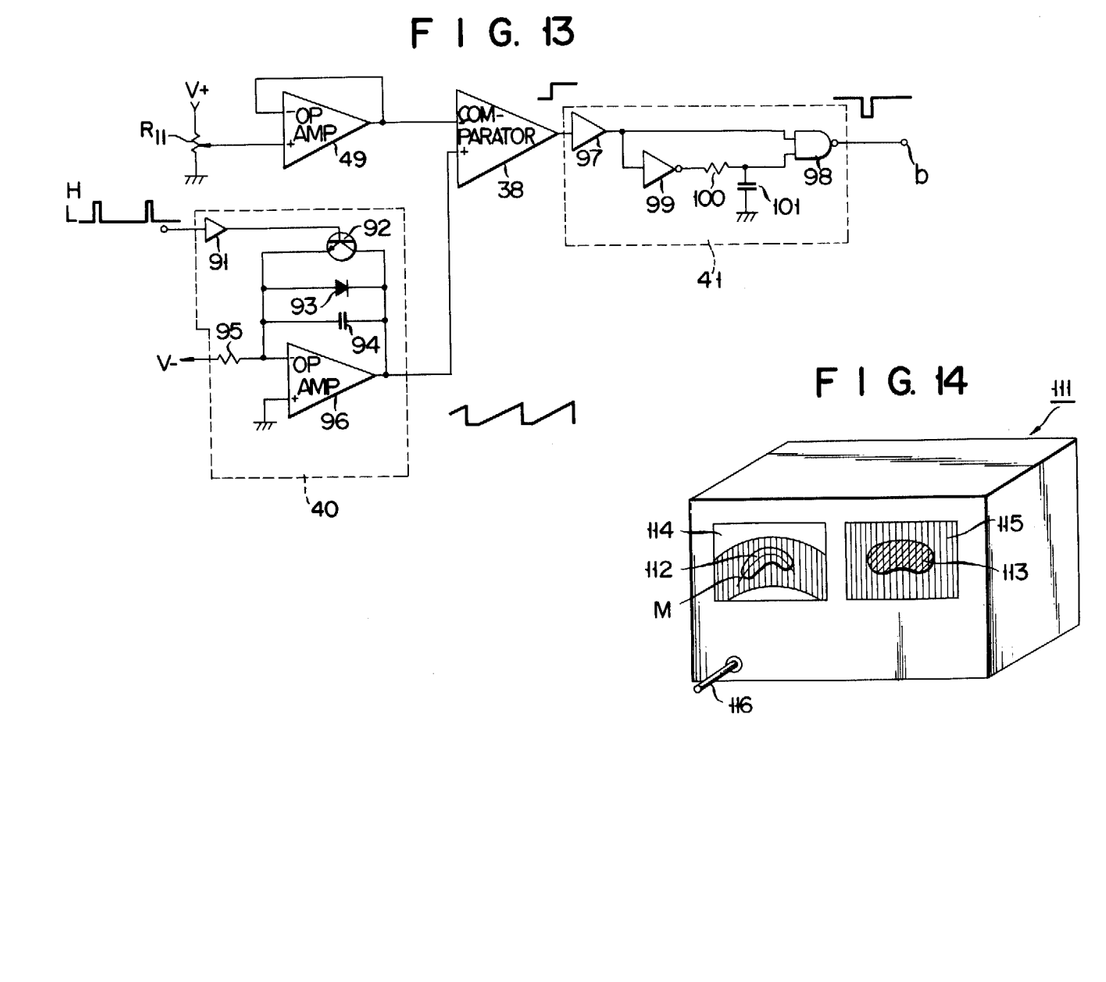
FIG. 13 shows a circuit diagram of the cross section setting circuit in FIG. 7.
FIG. 14 shows a perspective view of a major part of the ultrasonic diagnosing apparatus according to the invention.

The CRT display device 10 is provided to display the B-mode image 112 with the curve M set by the target cross-section setting circuit 11, as shown in FIG. 14.

Figure 7:
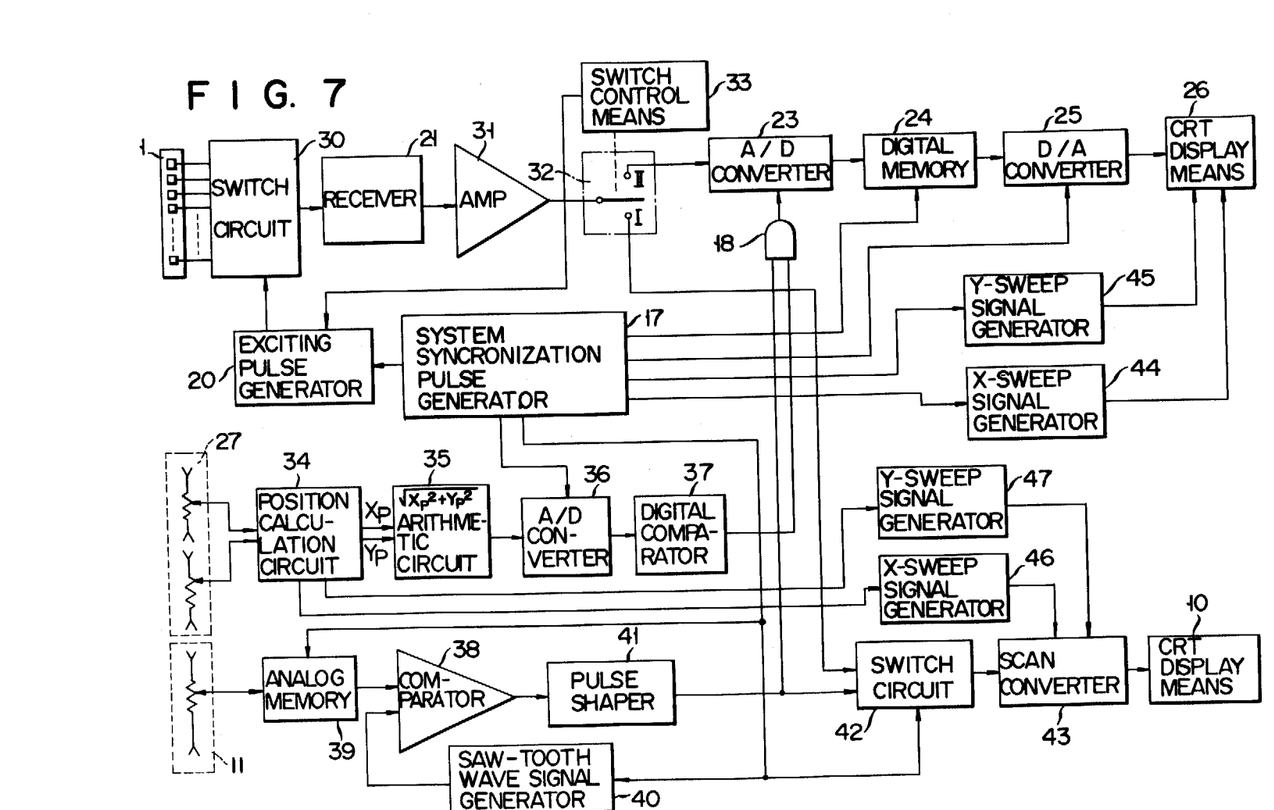
FIG. 7 shows a block diagram of another embodiment of the ultrasonic diagnosing apparatus according to the invention.

Reference is made further to FIGS. 8A to 8E illustrating wave forms in the circuits shown in FIG. 7. In operation, the switch 32 is first turned to the contact I so that the video signal (FIG. 8A) derived from the amplifier 31 is transferred through the switch circuit 42 to the scan converter 43. The video signal is converted into the B-mode video signal by the scan converter 43. The displays device 10 display the B-mode image 114 of the target portion as shown in FIG. 14.

An operator sets the cross section of the target section at a desired depth while observing the B-mode image on the CRT 10. The cross-section is manually set by the variable resistor in the target cross-section setting circuit 11. The data representing the desired depth of the target portion are stored in the memory 39. The stored data are read out from the memory 39 in synchronism with the pulse generation of the system synchronization pulse generator 17, and are supplied to the comparator 38. The comparator 38 is provided with a saw-tooth wave signal generated from the generator 40 in synchronism with a system synchronization pulse from the pulse generator 17. When these signals in the comparator 38 are coincident each other in level, an output signal is derived therefrom, which is in turned shaped by pulse shaper 41. The output signal representing the set depth of the target portion, after passing the switch 42, is supplied to the scan converter 43 and then is displayed on the CRT display device 10 in the form of a single line M (shown in FIG. 14) superposed on the B-mode image and indicating the depth of the target section desired to be diagnosed. The output signal from the pulse shaper 41 is also applied to one input terminal of the gate 18.

Figures 8A, 8B:
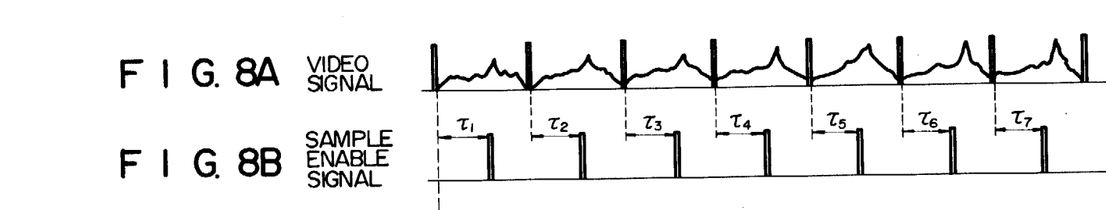
FIGS. 8A to 8F show a set of wave forms in various portions of the block diagram in FIG. 7.
Figure 8C:
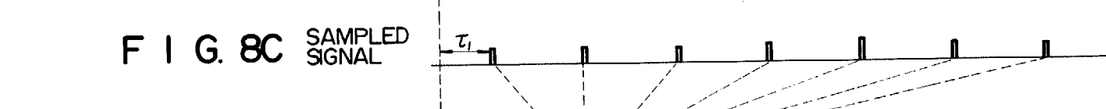

The position detection circuit 27, comprising a sine-cosine potentiometer, for example, produces position signals which in turn are applied to the position calculator 34 relative position (Xp, Yp) of the probe 1 is calculated. The distance $\sqrt{Xp^2+Yp^2}$ (representing the amount of movement of probe 1) from a reference point (the previous probe position defined in the orthogonal coordinates) to present the probe position is calculated by the arithmetic operation circuit 35. The $\sqrt{Xp^2+Yp^2}$ signal is then subjected to the AD conversion in the converter 36 so that the converted digital signal is compared with a reference signal designating a reference distance which determines the resolution of a modified C-mode image to be displayed by the CRT display device 26. Particularly, only lower several digits of $\sqrt{Xp^2+Yp^2}$ are compared with the reference signal. The lower several digits designate an amount of slight movement of the probe 1. Thus, comparison is made substantially between the amount of slight movement of the probe 1, designated by the lower several digits and the reference distance of the reference signal, and when these are coincident, the comparator 37 generates an output signal. The output signal is supplied to the other input terminal of the AND gate 18. Concurrent application of signals to both the input terminals of the gate 18 enables the gate 18 to produce a signal toward the A-D converter 23 as shown in FIG. 8B where $T_1$ through $T_7$ designate a time delay between the scanning signal and the system synchronization pulse. The output signal from the gate 18 serves as a sampling signal for the video signal of the A-D converter 23. The A-D converter 23 samples the output signal of the amplifier 31 to produce the signal shown in FIG. 8C and then converts the sampled signal into a digital signal which is in turn stored in a digital memory 24. The stored digital signal is read out from the memory 24 and supplied to the D-A converter 25 so that a D-A converter 25 converts the digital signal into an analog signal shown in FIG. 8D. The read/write operation of the memory 24 and the D-A converting operation are carried out under control of the system synchronization signal from the generator 17.

Figures 8D, 8E:
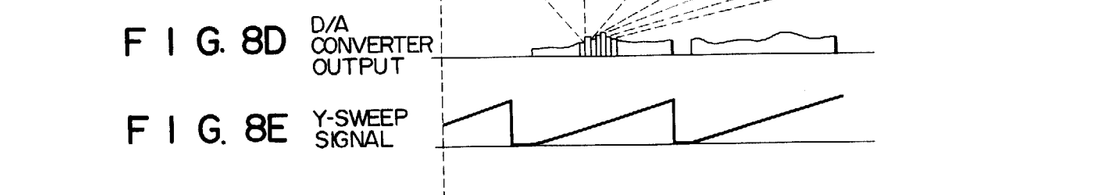
Figure 8F:
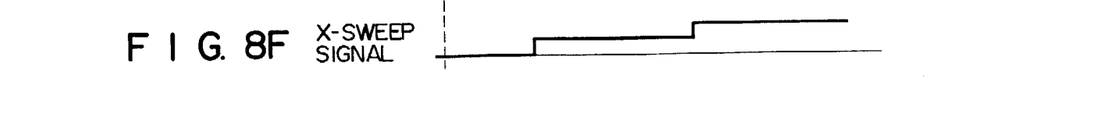

X- and Y-sweep signal generators 44 and 45 provide the CRT display device 26 with an X- and Y-sweep signals shown in FIGS. 8E and 8F, respectively. Therefore, the CRT display device 26 displays the modified C-mode image 113 of the desired target plane shown in FIG. 14.

Figure 9:
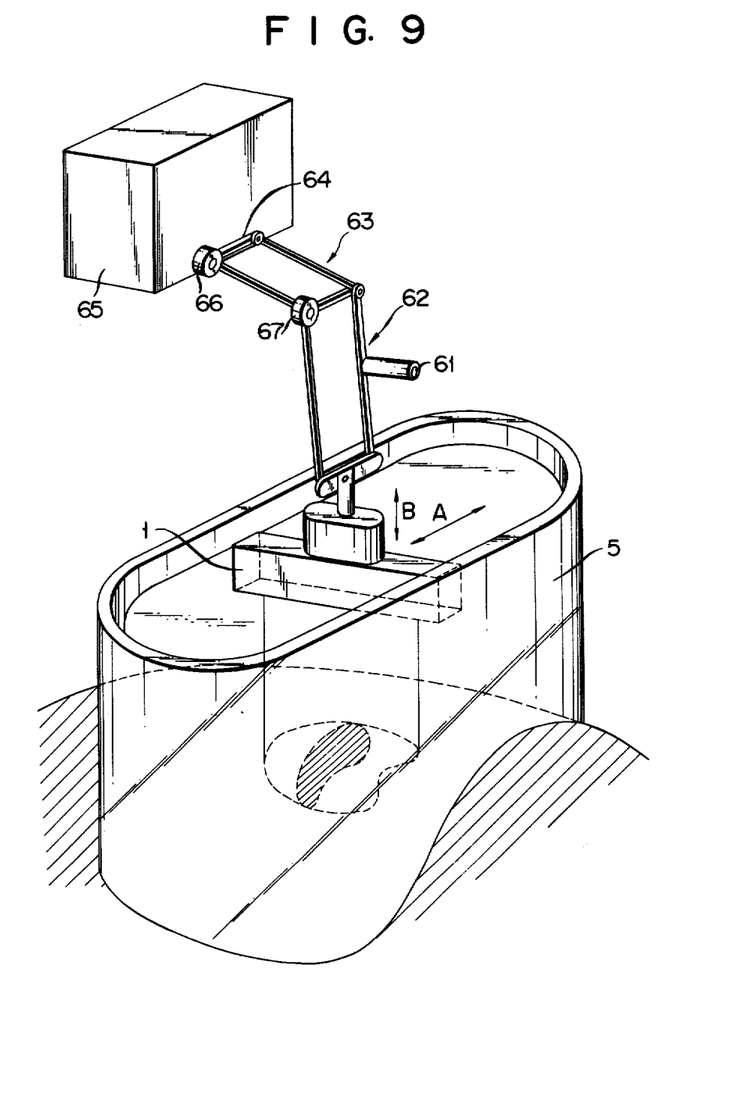
FIG. 9 structurally illustrates a probe driving mechanism and how the probe is handled practically.
Figure 10:
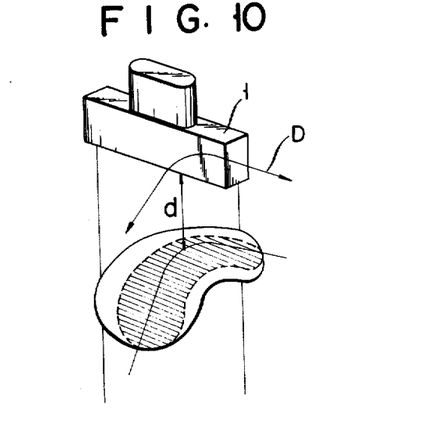
FIG. 10 illustrates how the probe moves with respect to a selected cross-section of the target portion to be diagnosed.

Another embodiment of the position detection of the probe 1 will be described hereinafter. The probe 1 is disposed being immersed in the water, for example, in the flexible bath 5 lying on the body to be diagnosed, as shown in FIG. 9. The probe 1 is manually moved by a handle 61, in this example. As shown, an arm 61 is attached to one of the arms forming a rectangular frame 62. Another rectangular frame 63 is operative in a pantograph fashion, being commonly coupled at one arm with the frame 62 and at another arm 64 in a fixing relation with a supporting member 65. The frame 63 is manually movable in directions indicated by arrows A and B with the handle 61. Accordingly, the probe 1 can move along a curve D shown in FIG. 10, wherein, character d designates a distance from the radiation surface of the probe 1 to the target cross-section. Sine-cosine potentiometers 66 and 67 are attached to two corners of the flexible frame 63.

Figure 11:
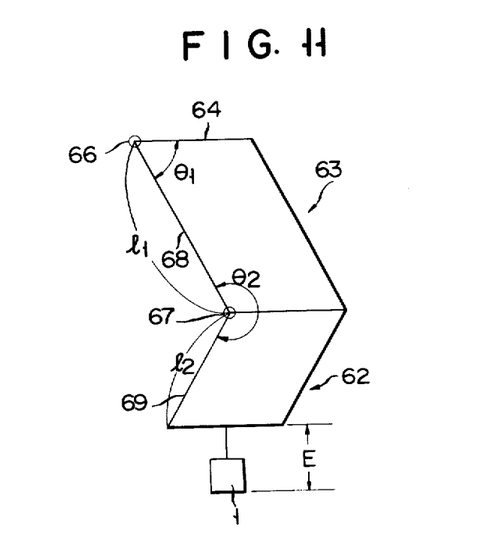
FIG. 11 illustrates the principles of the movement of the probe driving mechanism geometric shown in FIG. 9.

Turning now to FIG. 11 schematically illustrating the frames 62 and 63, a position (Xp, Yp) of the probe 1 is given below $$Xp \propto l_1 \cos\theta_1 + l_2 \cos\theta_2$$

$$Yp \propto l_1 \sin\theta_1 + l_2 \sin\theta_2 + E$$

In the above relations, $l_1$ is the length of the arm 68, $l_2$ the length of the arm 69, an angle between the arms 64 and 68; $\theta_1$; an angle between arms 69 and 70, $\theta_2$; the distance between the arm 71 and the ultrasonic radiation surface of the probe 1, E. The values of $\cos\theta_1$, $\cos\theta_2$, $\sin\theta_1$ and $\sin\theta_2$ are detected by means of the potentiometers 66 and 67.

Figure 12:
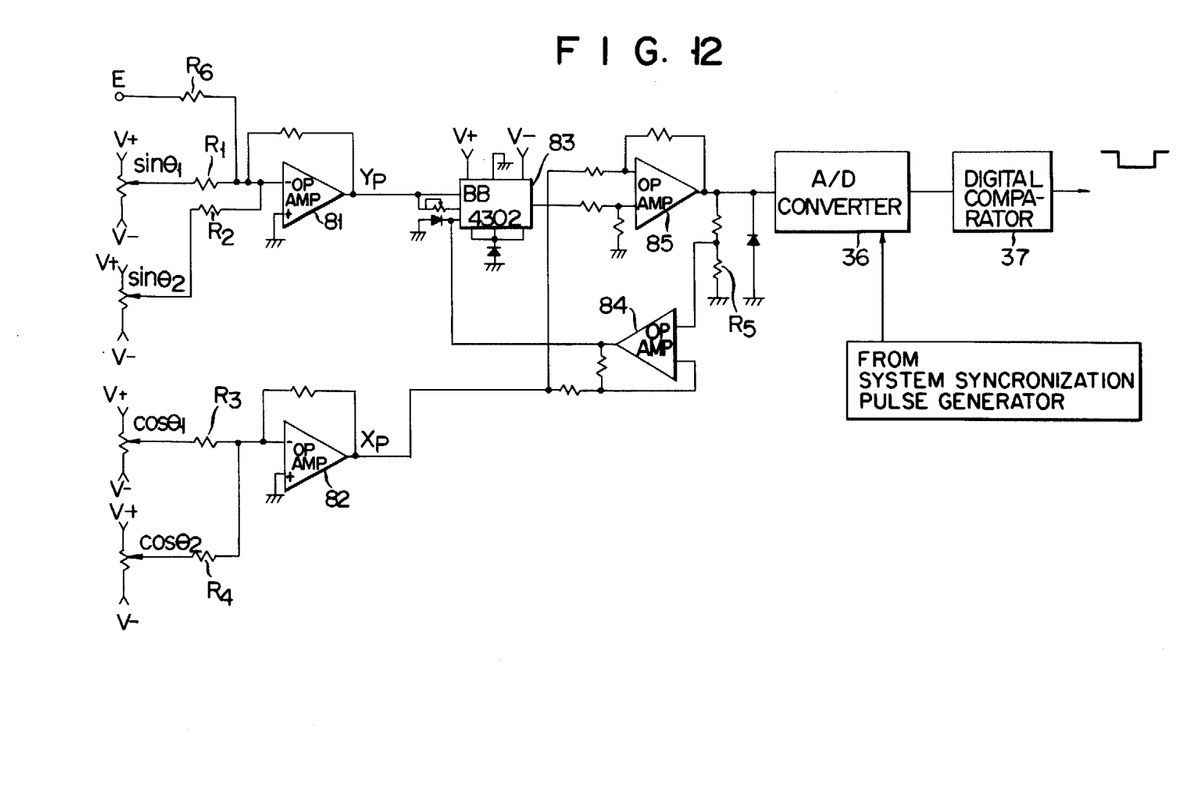
FIG. 12 shows a circuit diagram of the circuit block in FIG. 7 for detecting the actual position of the probe and for processing the position information.

Turning now to FIG. 12, there is shown a circuit for sampling the video signal delivered from the amplifier 31 shown in FIG. 7, depending on the position signal (Xp, Yp). Sin $\theta_1$ and sin $\theta_2$ signals detected by sine-cosine potentiometers 66 and 67 and the signal E representing the distance E are applied to an operational amplifier 81 serving as an adder, through weighting resistors R1, R2 and R6. Cosine $\theta_1$ and cosine $\theta_2$ signals detected by the same sine-cosine potentiometers are applied through weighting resistors R3 and R4 to another operational amplifier 82 also serving as an adder. The adder 81 produces a Yp-signal representing a position on Y-axis which in turn is applied to an arithmetic operation circuit 83.

The arithmetic operation circuit 83 may comprise an arithmetic operation circuit of BB4302 manufactured by Burr Brown Research Co., Ltd. The other adder 82 produces an Xp-signal representing a position on the X-axis of the probe 1 which is then applied to one input terminal of an operational amplifier 84 of which the other input terminal is connected through a resistor R5 to ground. The output signal from the amplifier 84 is transferred to the arithmetic operation circuit 83. The output signal of the arithmetic operation circuit 83 is inputted to the non-inverting terminal of an operational amplifier 85 of which the inverting input terminal receives the Xp-signal. Receiving these signals, the amplifier 85 produces a signal of $\sqrt{Xp^2+Yp^2}$ which is then applied to the A-D converter 36. Lower several digits of the $\sqrt{Xp^2+Yp^2}$ signal is compared with the reference digital signal designating the reference distance in the comparator 37 in order to produce the sampling signal.

The target cross-section setting circuit 11 will be described in detail with reference to FIG. 13. The cross-section of the target portion to be observed is set by properly sliding the slider terminal of a variable resistor R11. A signal with the potential determined by the sliding terminal position is supplied to the first operational amplifier 37 serving as a buffer amplifier. The output signal from the buffer 37 is applied to the first input terminal of the comparator 38 of which the second input terminal receives a saw-tooth wave signal from the saw-tooth wave pulse generating circuit 40. In actual practice an analog memory 39 (FIG. 7) is connected with the operational amplifier 49 and the comparator 38, but in this Figure it is omitted for ease of understanding. As shown, the circuit 40 comprises an inverter 91 receiving a rectangular wave pulse, a switching transistor 92 which is turned on and off in accordance with the output pulse of the inverter 91, a diode 93 and a capacitor 94 being connected across the collector-emitter path, a resistor 95 connecting at one end to the negative voltage source, and an amplifier 96 connecting at the inverting input terminal to the other end of the resistor 95 and the emitter of the transistor 92, at the non-inverting terminal to ground and at the output terminal to the collector of the transistr 92. The comparator 38 compares the output signal from the operational amplifier 39 with the saw-tooth wave signal from amplifier 96 and, when these are equal in level, produces a step-signal. The stepwise signal is wave-shaped in the wave-shaping circuit 41 to have a wave form with a short period. The wave shape circuit 41 comprises an inverter 97 for phase-inverting the output signal from the comparator 38, a NAND circuit 98 receiving at one input terminal the output signal from the inverter 97, a NOT circuit 99 and a resistor 100 inserted in series between the second input terminal of the NAND circuit 98 and the output terminal of the inverter 97, and a capacitor 101 connected between the second input terminal of the NAND circuit 98 and ground. In the circuit 41, the signal from the inverter 97 is directly applied to the first input terminal of the gate 98 without being delayed, and a signal delayed by the time constant determined by the resistor 100 and the capacitor 101 is applied to the second input terminal of the gate 98. As a result, the signal generated from the gate 98 goes negative by the time difference therebetween.

A major part of the outlook of the ultrasonic diagnosing apparatus according to the invention is illustrated in FIG. 14. On the front panel of a cabinet 111 of the apparatus are provided a display window 114 for displaying the B-mode image of the target to be diagnosed and another display window 115 for displaying the modified C-mode image of the target cross-section, which is set or selected by operating manually a joy switch 116 while observing the B-mode image on the window 114.

As described above, the ultrasonic diagnosing apparatus according to the invention can provide a modified of a desired target area so that the shape and the size of the target portion can be three dimensionally diagnosed.

What is claimed is:

1. An ultrasonic diagnosing apparatus comprising:
   a probe having a plurality of transducer means for radiating ultrasonic beams toward an object to be examined and for converting ultrasonic echoes into electrical echo signals;
   first display means for displaying a B-mode image of the object;
   means for setting a selected C-mode cross-section to be observed and diagnosed while observing said B-mode image;
   means for storing data representing the selected C-mode cross-section set by said setting means;
   means for detecting the position of said probe;
   means for producing control signals responsive to signals from said storing means and said detection means;
   means responsive to said control signals for moving said transducer means with respect to the object;
   means responsive to said control signals for electronically driving said transducer means to scan the selected C-mode cross-section;
   means responsive to said control signals for processing said electrical echo signals converted by said transducer means to produce electrical signals representing the selected C-mode cross-section;
   memory means responsive to said control signals for storing the electrical signals representing the selected C-mode cross-section; and
   second display means coupled with said memory means for displaying an image of the selected C-mode cross-section of the object.

2. The ultrasonic diagnosing apparatus of claim 1 wherein said control signal producing means includes a system synchronization pulse generator, a delay function generator, and a gate circuit coupled with said delay function generator.

3. The ultrasonic diagnosing apparatus of claim 2 wherein said means for processing said electrical echo signals includes a sampling circuit coupled with said gate circuit.

4. An ultrasonic diagnosing apparatus comprising:
   a probe with transducer means for radiating ultrasonic beams toward an object to be examined and for converting ultrasonic echoes into electrical echo signals;
   first display means for displaying a B-mode image of the object,
   means for setting a selected C-mode cross-section to be observed and diagnosed while observing said B-mode image;
   first storage means for storing data representing the selected C-mode cross-section set by said setting means;
   means for generating a system synchronization pulse;
   means for generating a pulse in synchronism with the system synchronizing pulse to excite the transducer means of the probe thereby to produce ultrasonic waves;
   means for receiving the reflected waves from the target portion;
   position detection means for detecting the position of the probe;
   a delay function generator responsive to position data generated by said first storage means and said position detection means for producing a delay control signal with a predetermined delay time representing a diagnostic area of the target;
   means for moving said transducer means with respect to the object in accordance with the delay control signal;
   a sampling circuit responsive to said delay control signal for sampling the echo signals corresponding to the selected C-mode cross-section of the object;
   an analog-to-digital converter for converting the output signal from said sampling circuit into a corresponding digital signal;
   a second storage means for storing the output signal from said analog-to-digital converter;
   a digital-to-analog converter for converting the signal read out from said second storage means into a corresponding analog signal; and
   second display means, coupled with said digital-to-analog means for displaying a modified C-mode image of the object.

5. The ultrasonic apparatus of claim 4 further comprising means for amplifying selected electrical echo signals.

6. The ultrasonic diagnosing apparatus of claim 4 further comprising a gate circuit responsive to the delay control signal for permitting the system synchronizing pulse to selectively pass therethrough.

7. An ultrasonic diagnosing apparatus comprising:
   a probe having a plurality of transducer means for radiating ultrasonic beams toward an object to be examined and for converting ultrasonic echoes into electrical echo signals;
   first display means for displaying a B-mode image of the object;
   detection means for detecting the actual position of the probe;
   setting means for setting a selected C-mode cross-section to be observed and diagnosed while observing said B-mode image;
   sampling means for selecting the electrical echo signals corresponding to the selected C-mode cross-section of the object which are included in the output signals delivered from said probe;

means for converting the output signals of said sampling means into digital signals;

means for storing said digital signals;

means for converting the digital signals from said storing means into analog signals; and second display means coupled with said converting means for displaying a modified C-mode image of the object.

8. An ultrasonic diagnosing apparatus according to claim 7, wherein said sampling means includes a gate which is enabled when it simultaneously receives output signals from said detection means and said setting means.

9. An ultrasonic apparatus according to claim 7, wherein said detection means includes first means for calculating the coordinates of the probe in an orthogonal coordinate system, second means for calculating the distance of the calculated coordinates from the previous position of said probe; and means for comparing the output signal of said second calculating means with a reference signal designating a reference distance.

10. An ultrasonic apparatus according to claim 7, wherein said cross-section setting means includes means for producing a depth signal representing the depth of the selected C-mode cross-section; means for storing the depth signal; means for generating a saw-tooth wave signal; means for comparing the output signal of said saw-tooth wave signal generator with the depth signal; and means for wave-shaping the output signal from said comparator.

11. An ultrasonic diagnosing apparatus for displaying a modified C-mode image of an object taken at a selected cross-sectional plane defined by a trace line displayed on a B-mode image of the object comprising:

an electronic linear scanning probe having a plurality of transducer means for radiating ultrasonic beams toward the object to be examined and for converting reflected ultrasonic echoes into electrical echo signals;

means for displaying a B-mode image of the object;

means for setting and displaying a desired trace line on said B-mode image, said trace line defining a selected C-mode cross-section to be observed and diagnosed while observing said B-mode image;

first storage means for storing data representing the selected C-mode cross-section set by said setting means;

means for detecting the position of the probe;

means coupled with daid first storage means and said detection means for producing control signals responsive to the signals from said first storage means and said detection means;

means responsive to said control signals for moving said probe with respect to the object;

means responsive to said control signals for electronically driving said transducer means to scan ultrasonically the target;

means responsive to said control signals for receiving and sampling the electrical echo signals from said transducer to form video signals representing said selected C-mode image;

memory means for storing said video signals;

second display means for displaying the selected C-mode image of the object.

12. The ultrasonic diagnosing apparatus of claim 11 wherein said means for producing control signals includes a system synchronization pulse generator, a delay function generator and a gate circuit.

13. The ultrasonic diagnosing apparatus of claim 12 wherein said means for electronically driving said transducer means includes an exciting pulse generator which applies exciting pulses to the transducer means in synchronism with the pulse of the system synchronization pulse generator.

14. The ultrasonic diagnosing apparatus of claim 12 wherein said means for receiving and sampling includes a sampling circuit.

15. An ultrasonic diagnosing apparatus for displaying a modified C-mode image of an object taken at a selected cross-section defined by a trace line displayed on a B-mode image of the object comprising:

a probe with a plurality of transducer means for radiating ultrasonic beams toward an object to be examined and for converting ultrasonic echoes into electrical echo signals;

a system synchronization pulse generator;

an exciting pulse generator which produces pulses in synchronism with the pulses of said system synchronization pulse generator to thereby excite the transducer means to radiate ultrasonic rays;

a receiver for selectively receiving the ultrasonic echo signals from the probe;

a first switch means coupled with said system synchronization pulse generator for selectively feeding the exciting pulses from said exciting pulse generator to the probe and carrying echo pulses reflected from the probe to said receiver;

an amplifier for amplifying the output signal from said receiver;

a second switch means for switching the output signal from said amplifier toward either a first display means to display a B-mode image or to a second display means to display a C-mode image;

a first display means coupled with said second switch means for displaying a B-mode image of the target;

means for setting a desired trace line on said B-mode image, said trace line defining a selected C-mode cross-section to be observed and diagnosed while observing said B-mode image;

a first memory for storing the output signal from said setting means;

a first analog-to-digital converter for converting the output signal from said amplifier into a digital signal when said second switch feeds the output signal from said amplifier toward said second display means;

a second memory for storing the output signal from said first analog-to-digital converter;

a position detection means for detecting the position of said probe;

a calculation circuit coupled with said position detection means for calculating the position of said probe;

an arithmetic operation circuit coupled with said calculation circuit for calculating the movement of the probe from a reference point;

a second analog-to-digital converter for converting the output signal from said arithmetic operation circuit into a digital signal;

a first comparator for comparing the output signal from said arithmetic operation circuit with a reference signal representing a reference distance;

a saw-tooth wave generator for generating saw-tooth wave signals in synchronism with pulses generated by the system synchronization pulse generator;

a second comparator for comparing the output signal from said second memory with the saw-tooth wave signal;

a pulse shaper for wave-shaping the output signal from said comparator;

a gate circuit for passing a control signal to said first analog-to-digital converter when it receives simultaneous signals from said first comparator and said wave-shaper;

a digital-to-analog converter for converting the signal from said first memory into an analog signal; and a second display means coupled with said digital-to-analog converter for displaying a desired C-mode image taken along the trace line set by said first display means.

* * * * *